(12) United States Patent
Burns

(10) Patent No.: US 8,800,552 B2
(45) Date of Patent: Aug. 12, 2014

(54) TRACHEAL TUBE AND TUBE EXTENSION

(75) Inventor: John P. Burns, Longmont, CO (US)

(73) Assignee: Covidien LP, Mansfield, MA (US)

( * ) Notice: Subject to any disclaimer, the term of this patent is extended or adjusted under 35 U.S.C. 154(b) by 560 days.

(21) Appl. No.: 12/638,234

(22) Filed: Dec. 15, 2009

(65) Prior Publication Data

US 2011/0139151 A1 Jun. 16, 2011

(51) Int. Cl.
*A61M 16/08* (2006.01)

(52) U.S. Cl.
USPC ............ 128/202.27; 128/200.24; 128/207.14; D24/110.1

(58) Field of Classification Search
USPC .......................... 128/200.24, 202.27, 207.14; D24/110.1; 604/523
See application file for complete search history.

(56) References Cited

U.S. PATENT DOCUMENTS

| | | | |
|---|---|---|---|
| 3,388,705 A | 6/1968 | Grosshandler | |
| 4,235,229 A | 11/1980 | Ranford et al. | |
| 4,852,564 A * | 8/1989 | Sheridan et al. | ......... 128/202.27 |
| 5,443,064 A | 8/1995 | Theis et al. | |
| 5,803,064 A | 9/1998 | Phelps et al. | |
| 6,951,218 B2 | 10/2005 | Gradon et al. | |
| 6,994,088 B2 | 2/2006 | Briggs, III | |
| 2004/0154623 A1 | 8/2004 | Schaeffer et al. | |
| 2008/0041391 A1 * | 2/2008 | Worley | ................... 128/207.14 |
| 2008/0142003 A1 | 6/2008 | Depel | |
| 2008/0257357 A1 | 10/2008 | Schwartz et al. | |

FOREIGN PATENT DOCUMENTS

GB 649230 A 1/1951

OTHER PUBLICATIONS

International Search Report and Written Opinion for PCT Application No. PCT/US2010/059810 dated May 18, 2011, 18 pgs.
www.teleflexmedical.com; Rusch Easytube Double Lumen; 9 pages.
www.arcadiamedical.com; Silicone Cuffless and Silicon Cuffless Extended Connect Pediatric & Neonatal Tracheostomy Tubes; 2 pages.

* cited by examiner

*Primary Examiner* — Laura Bouchelle
(74) *Attorney, Agent, or Firm* — Fletcher Yoder PC

(57) ABSTRACT

The present disclosure describes systems that may extend the proximal length of a tracheal tube. A tracheal tube extension system may be provided that includes secure attachment features used to securely couple a tracheal tube to a tracheal tube extension. The tracheal tube extension may be attached to the proximal end of the tracheal tube and includes an upper end connector. The upper end connector may be used to couple the tracheal tube extension to a variety of medical devices such as a ventilator, a manual respirator, a nebulizer, a vaporizer, suctioning equipment, and so forth. The use of the tracheal tube extension enables an increase in working space in the area in front of the tracheal tube, thus allowing for the convenient and rapid access to the various connectors that may be coupled to the patient.

21 Claims, 4 Drawing Sheets

TRACHEAL TUBE AND TUBE EXTENSION

BACKGROUND

The present disclosure relates generally to tracheal tubes and, more particularly, to tracheal tubes with proximal extensions.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Tracheal tubes may be utilized to define a clear passageway for air, other gases, and medicaments to the trachea and lungs, thus providing an artificial airway for spontaneous or mechanical ventilation of a patient. Such tracheal tubes may include endotracheal tubes and tracheastomy tubes. Tracheostomy tubes, for example, are typically introduced into an opening or stoma in front of the neck and trachea. The stoma is defined by a tracheotomy incision in the neck that provides access to the trachea. When the inner or distal end of the tracheostomy tube is properly inserted into the trachea, the outer or proximal end will extend from the neck a certain distance. The proximal end of the tracheostomy tube may include a connector to attach various devices such as ventilators, manual respirators, suctioning equipment, nebulizers, vaporizers, and so forth. However, in certain circumstances such as with prone patients and with neonatal or pediatric patients, the attachments at the proximal end of the tracheal tube may come into contact with the neck, chin, or stoma, potentially interfering with patient comfort and mobility.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

Figure 1:
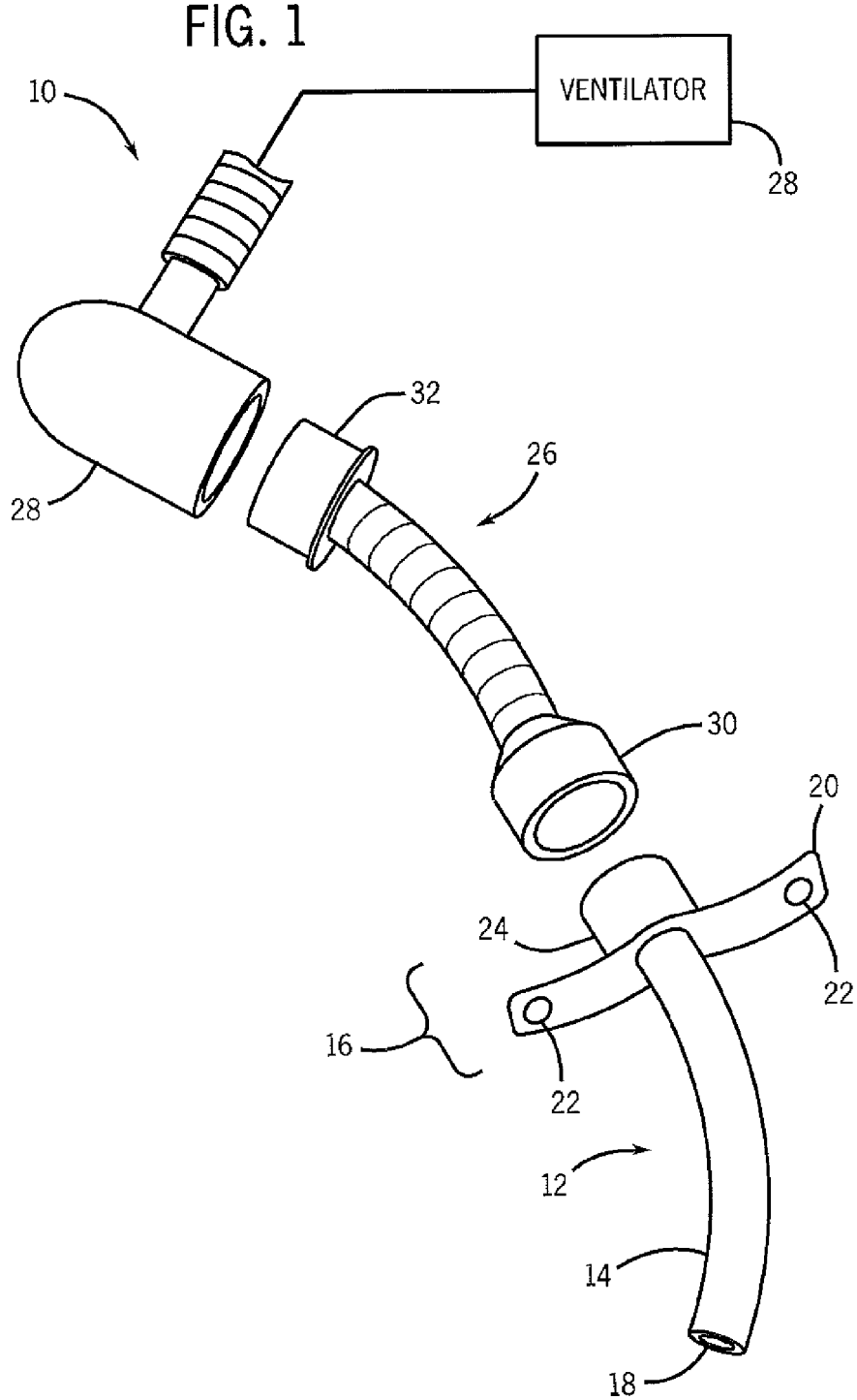
FIG. 1 illustrates an embodiment of an artificial airway management system.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The disclosed embodiments include medical devices for artificial airway applications. In certain embodiments, a tracheal tube extension is provided that extends from the proximal end of a tracheal tube. The tracheal tube extension provides a clinician with an increased working space in the area in front of the tracheal tube, thus allowing for rapid attachment of devices such as ventilators, manual respirators, suctioning equipment, nebulators, vaporizers, tee connectors, and so forth, to the proximal end of the tracheal tube. Further, the tracheal tube extension may decrease patient discomfort during regular use by extending the distance between attachments to the tracheal tube and the frontal neck region. The increased distance provides for additional freedom of movement of the head and minimizes physical contact between the chin, stoma, and/or neck with the attachments at the proximal end of the tracheal tube. Additional comfort in a prone position is also realized by extending the attachments to the tracheal tube so that they may lie, for example, on the chest instead of on the neck.

In certain embodiments, the tracheal tube extension may incorporate attachment features that securely hold the tracheal tube extension in place but that also allow for the easy removal of the tracheal tube extension. Accordingly, the tracheal tube extension may be easily removed for extubation and before the patient undergoes certain clinical procedures, such as magnetic resonance imaging (MRI). Such attachment features also enable the rapid removal of the tracheal tube extension during emergencies and the rapid attachment to other medical equipment, e.g., suctioning equipment, or manual respirators. In other embodiments, the tracheal tube extension system is manufactured of materials that are MRI compatible, thus allowing for the use of the tracheal tube extension during MRI procedures. The disclosed embodiments may also include devices designed to minimize airway dead space of the system, i.e., the volume of air that is aspirated by the patient during inhalation but that does not participate in gas exchange. Minimizing airway dead space allows for less energy expenditure and result in a decreased work-of-breathing (WOB).

With the foregoing in mind, FIG. 1 depicts an embodiment of airway management system 10 that may be utilized to provide respiratory support in a patient. A tracheostomy incision is typically made in the patient trachea and a tracheal tube 12 is inserted into the trachea. The tracheal tube 12 includes a distal end portion 14 and a proximal end portion 16. The distal end portion 14 is inserted into the trachea and typically includes a curved portion so as to comfortably fit inside the patient airway. In certain embodiments, the outer diameter (OD) of the distal end portion 14 may be approximately 1 mm-20 mm, which may vary depending on whether the patient is a neonatal patient, a pediatric patient or an adult patient. The distal end portion 14 may be any suitable length. For example, the distal end portion 14 may be 50 mm-175 mm. A distal opening 18 may be beveled to allow for smoother insertion through the larynx and trachea. The tracheal tube 12 may also include any suitable number of lumens that may be appropriately sized and shaped for inflation, deflation, or suction.

The tracheal tube may include a neck flange 20 that supports the tracheal tube 12 and allows the tracheal tube 12 to be securely attached to the neck of the patient. The neck flange 20 may include flange holes 22 that allow a neck band to be placed circumferentially around the neck and attached to the flange holes 22, thus securing the tracheal tube 12 to the patient. A proximal end connector 24 extends axially from the neck flange 20 and may be used to couple a variety of medical devices, such as a tracheal tube extension 26, to the tracheal tube 12. In certain embodiments, the proximal end connector 24 may include a 15 mm outer diameter portion, i.e., male end connector that can couple with a standard 15 mm inner diameter (ID) connector, i.e., female end connector. The use of a standard outer diameter size, such as 15 mm, for the upper end connector 32 allows for a variety of medical devices such as a tracheal tube extension 26, a ventilator 28, a manual respirator, suctioning equipment, and so forth, to be connected to the tracheal tube 12. It is to be understood that in other embodiments, the proximal end connector 24 may include a male connector portion of a different size, for example, 8 mm OD, 8.5 mm OD, and so on.

As mentioned above, the tracheal tube extension 26 may be attached to the tracheal tube 12 by coupling a lower end connector 30 of the tracheal tube extension 26 to the proximal end connector 24 of the tracheal tube 12. The lower end connector 30 may include a female connector portion, such as 15 mm ID portion, that can couple with the corresponding 15 mm OD proximal end connector 24. The lower end connector 30 may also include secure attachment features such as those described in more detail with respect to FIG. 2 below, that secure the coupling between the tracheal tube 12 and the tracheal tube extension 26. Once attached to the proximal end connector 24, the tracheal tube extension 26 is used to extend the proximal length of the tracheal tube 12 by including the upper end connector 32 placed at a length, such as 100 mm, axially from the neck flange 20. It is to be understood that other length extensions, such as 50 mm, 150 mm, 175 mm, and so forth, may be used. The upper end connector 32 may include a 15 mm outer diameter portion, i.e., male end connector that can couple with a standard 15 mm inner diameter (ID) connector, i.e., female end connector, thus allowing for a variety of medical devices to extendably couple to the tracheal tube 12.

The use of the tracheal tube extension 26 may be advantageous because it provides a clinician with an increased working space in the area in front of the tracheal tube 12, thus allowing for convenient and rapid access to the various connectors that may be coupled to the upper end connector 32. Further, patient comfort is enhanced because the tracheal tube extension 26 minimizes physical contact between the chin, stoma, and/or neck with the attachments at the proximal end of the tracheal tube 12. The patient may thus be able to move more freely without contacting the connectors that may be attached at the proximal end of the tracheal tube 12.

Figure 2:
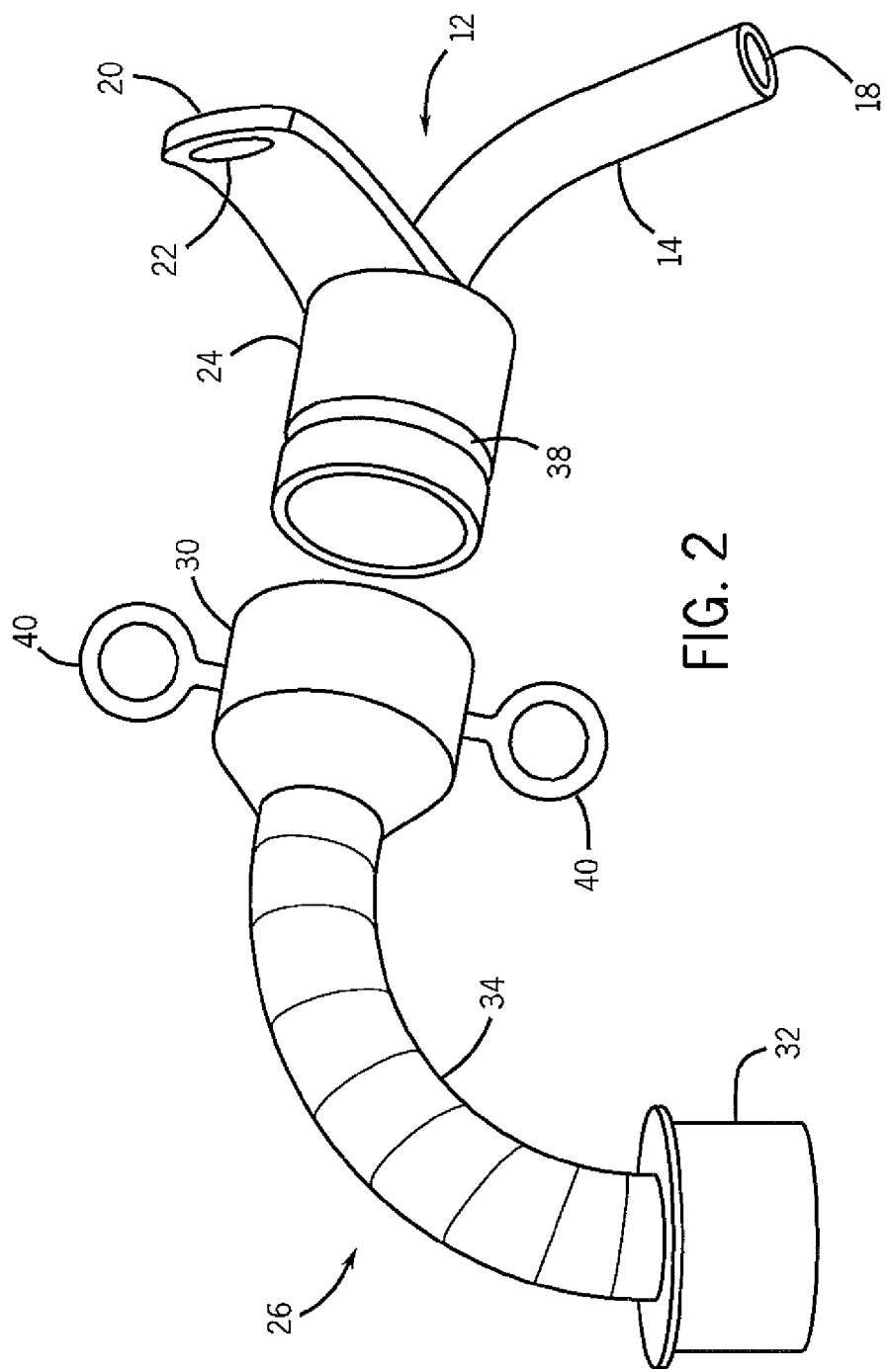
FIG. 2 is a perspective view depicting an embodiment of a tracheal tube extension and an embodiment of a tracheal tube.

Turning to FIG. 2, the figure is a perspective view of an embodiment of the proximal tube extension 26 and the tracheal tube 12. The tracheal tube extension 12 includes an intermediate portion 34 that couples the lower end connector 30 with the upper end connector 32 and forms a passage for air and other substances. In certain embodiments, the intermediate portion 34 is reinforced so as to prevent kinking, i.e., occlusion, of the tracheal tube extension 26. In certain embodiments, the reinforced intermediate portion 34 may include a wire or other element positioned inside the walls of the intermediate portion 34 and wound circumferentially around the inner chamber of the intermediate portion 34. The reinforcement allows for the flexible bending of the intermediate portion 34 but prevents the formation of a kink in the inner chamber of the intermediate portion 34. Non-spiral wound reinforcements and reinforcements of other configurations may also be envisioned. In other embodiments, the reinforced intermediate portion 34 may include a corrugated flexible tubing having a ribbed outer surface and manufactured out of a material that is MRI compatible. Indeed, in certain embodiments, all the components of the tracheal tube extension 26 may be MRI compatible components, resulting in an MRI compatible tracheal tube extension 26. An MRI compatible tracheal tube extension 26 allows the use of the tracheal tube extension inside an MRI scanner without affecting the image quality as described in more detail with respect to FIG. 6 below.

As mentioned above, the tracheal tube 12 may be placed inside the trachea of a patient and secured to the trachea by placing a neck band circumferentially around the neck and attaching the neck band to the flange holes 22 of the flange 20. The proximal end connector 24 of the tracheal tube 12 may then be coupled to the lower end connector 30 of the tracheal tube extension 26. In certain embodiments, both the proximal end connector 24 and the lower end connector 30 may include secure attachment features that prevent the connectors 24, 30 from decoupling during use. Indeed, such secure attachment features allow for the tracheal tube extension 26 to stay firmly coupled to the tracheal tube 12 during normal use of the tracheal tube extension 26. In one embodiment, the proximal end connector 24 includes a recess 38 in the body of the proximal end connector 24. The recess 38 may allow various secure attachment features such as extensions or protrusions, such as in the form of a barb or a peg included in the lower end connector 30 to enter the recess 38 and to securely engage the recess 38 so as to prevent inadvertent decoupling of the tracheal tube extension 26 from the tracheal tube 12. In order to rapidly decouple the tracheal tube extension 26 from the tracheal tube 12, certain embodiments include a set of rings 40 or other manually grippable features protruding from the sides of the lower end connector 30 and described in more detail below with respect to FIG. 3.

Figure 3:
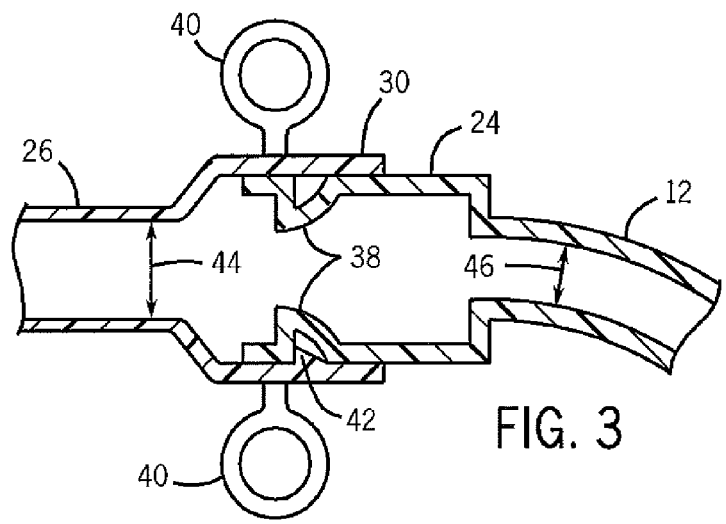
FIG. 3 is a schematic view depicting an embodiment of a tracheal tube extension coupled to an embodiment of a tracheal tube.

FIG. 3 illustrates a cross-section of an embodiment of the tracheal tube extension 26 coupled to an embodiment of the proximal end connector 24. Both the tracheal tube extension 26 and the proximal end connector 24 include secure attachment features 38, 42. As mentioned above with respect to FIG. 2, the proximal end connector 24 includes a recess 38 positioned circumferentially around the proximal end connector 24. In the illustrated embodiment, the recess 38 has a single barb 42 lodged inside of the recess 38. The barb 42 may be included in the interior wall of the lower end connector 30. In certain embodiments, multiple barbs 42 may be included in the interior wall of the lower end connector 30. When the proximal end connector 24 is inserted into the lower end connector 30, the barbs 42 may exert a radial force perpendicular to the walls of the lower end connector 30. The radial force may cause the walls of the lower end connector 30 to expand outwardly. When the proximal end connector 24 reaches a certain distance inside the lower end connector 30, the barbs 42 encounter the recess 38 and enter into the recess 38. Once inside the recess 38, the barbs 42 may no longer exert a radial force, thus causing the lower end connector 30 to contract and form a tight and secure coupling with the proximal end connector 24.

The proximal end connector 24 depicted in FIG. 3 may also be coupled to a standard female connector, i.e., a connector such as a 15 mm ID female connector that does not have any secure attachment features. The outer wall of the proximal end connector 24 may not extend beyond a standard size, for example, 15 mm OD, and therefore the proximal end connector 24 is compatible with standard connectors, such as a 15 mm ID female connector. This compatibility feature exhibited by the proximal end connector 24 allows for the decoupling of the tracheal tube extension 26 and the coupling of a variety of medical devices, e.g., manual respirators, suctioning equipment, nebulizers, and so forth. Accordingly, it may not be necessary to extubate the patient when switching to a female connector that has no secure attachment features.

In certain embodiments, the rings 40 may be provided that enhance the ability of a clinician to rapidly and comfortably decouple the tracheal tube extension 26 from the tracheal tube 12. The clinician may first grasp the rings 40 and pull on the rings 40 in a lateral direction, i.e., perpendicular from an axis extending through the center of the opening of the lower end connector 30, so that the pulling force on each ring 40 is directed away from the opposite ring 40. By pulling in opposite lateral directions, the clinician may rapidly disengage the barb 42 from the recess 38. The clinician may then pull the rings 40 in an axial direction away from the patient's trachea in order to decouple the tracheal tube extension 26 from the tracheal tube 12.

In certain embodiments, such as that depicted in FIG. 3, an inner diameter 44 of the tracheal tube extension 26 has a different size from an inner diameter 46 of the tracheal tube 12. As depicted, the larger diameter of the tracheal tube extension 26 may allow for enhanced resistance to kinking as well as for easier grasping and manipulation of the tracheal tube extension 26. In other embodiments, the inner diameter 44 of the tracheal tube extension 26 has the same size from the inner diameter 46 of the tracheal tube 12. By having substantially the same inner diameters 44, 46, the dead space of the airway management system 10 is minimized. Dead space results from having a volume of air larger than the volume of air that regularly participates in a gas exchange in the lungs, i.e., oxygen and carbon dioxide exchange. Further, the inner diameter 46 of the tracheal tube 12 may have been specifically chosen to achieve a certain work-of-breathing and translaryngeal airflow. Accordingly, the inner diameter 44 of the tracheal tube extension 26 may be chosen to match the inner diameter 46 of the tracheal tube 12, and thus achieve the same work-of-breathing and translaryngeal airflow. In other embodiments, the inner diameter 44 of the tracheal tube extension 26 may be smaller than the inner diameter 46 of the tracheal tube 12. Such embodiments may be chosen to further minimize the dead space and work-of-breathing of the patient. It is to be noted that any number of inner diameters 44, 46 sizes may be used. Indeed, the inner diameters 44, 46 may range from approximately 1 mm to upwards of 20 mm.

Figure 4:
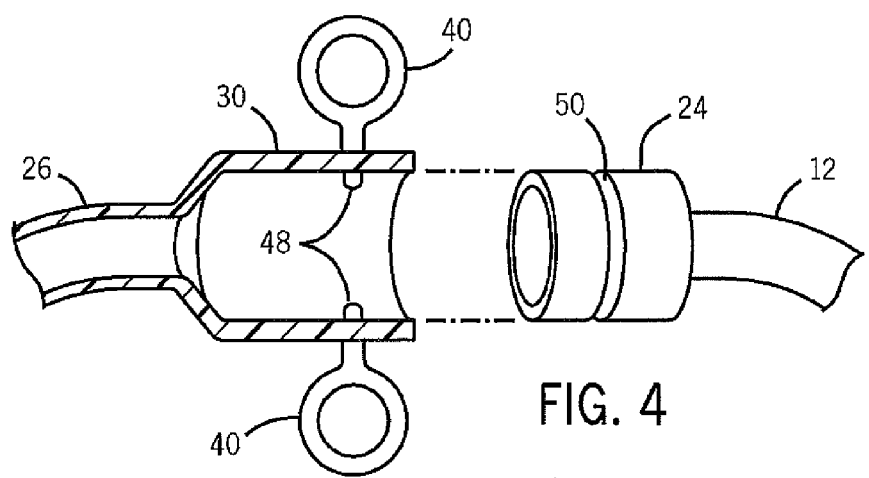
FIG. 4 is a is schematic view depicting another embodiment of a tracheal tube extension coupled to an embodiment of a tracheal tube.

Turning to FIG. 4, a cross-section is illustrated of an embodiment of the proximal end connector 24 along with a perspective view of an embodiment of the tracheal tube 12. The proximal end connector 24 and the lower end connector 30 depicted in FIG. 4 includes other embodiments of the secure attachment features, namely a pair of pegs 48, that may enter a groove 50 of the proximal end connector 24. In one embodiment, each peg 48 is disposed inside a peg recess in the inner wall of the lower end connector 30 and includes a peg spring positioned inside each peg 48. The peg spring may cause the peg 48 to extend outwardly from the peg recess. As the proximal end connector 24 is slid into the lower end connector 30, each peg 48 encounters the outer wall of the proximal end connector 24. The peg 48 may then move inside the peg recess, thus increasing the compression of the peg spring. Once the proximal end connector 24 is slid a certain distance into the lower end connector 30, the peg 48 may encounter the groove 50. The peg 48 may then enter the groove 50 by virtue of the peg spring propelling the peg 48 upwards into the groove 50.

In another embodiment, each peg 48 is disposed on the surface of the inner wall of the lower end connector 30 and is not recessed. In this embodiment, as the proximal end connector 24 is slid into the lower end connector 30, each peg 48 encounters the outer wall of the proximal end connector 24 and may exert a radial force in a direction perpendicular and away from the walls of the lower end connector 30. The radial force may cause the lower end connector 30 to expand outwardly. Once the proximal end connector 24 is slid a certain distance into the lower end connector 30, the peg 48 may encounter the groove 50 and enter the groove 50. Once inside the groove 50, the peg 48 may no longer exert a radial force, thus causing the lower end connector 30 to contract and form a tight and secure coupling with the proximal end connector 24.

The secure attachment features depicted in FIGS. 3 and 4 allow for the tracheal tube extension 26 to stay firmly coupled to the tracheal tube 12 during normal use. It is to be understood that other attachment features may be used. For example, a peg-like extension, a ring-like extension, or a partial ring-like extension may be used to enter the recess 38 or the groove 50 to securely couple the tracheal tube extension 26 to the tracheal tube 12. Further, the disclosed embodiments may also include embodiments that contain no secure attachment features, such as the embodiments described in more detail with respect to FIG. 5 below.

Figure 5:
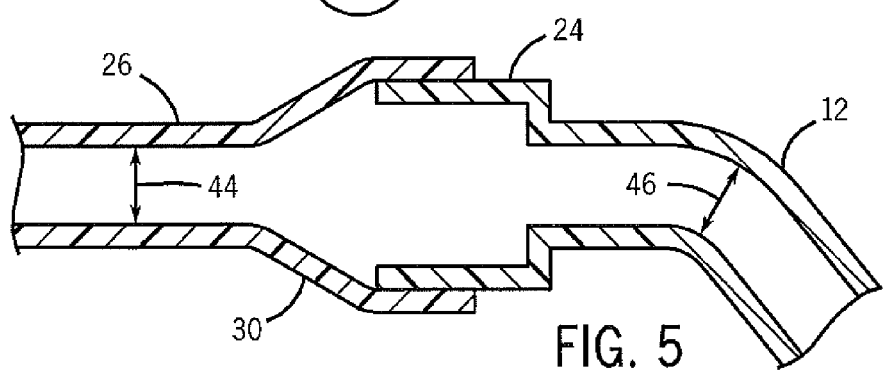
FIG. 5 is a schematic view of an embodiment of a tracheal tube extension and a perspective view of an embodiment of a tracheal tube.

FIG. 5 is a schematic view of an embodiment of the tracheal tube extension 26 coupled to an embodiment of the proximal end connector 24 where neither the tracheal tube extension 26 nor the proximal end connector 24 include secure attachment features. In these embodiments, the attachment feature may be provided by an interference fit, i.e., press fit, between lower end connector 30 and the proximal end connector 24. The proximal end connector 24 is pressed into the lower end connector 30, which may cause a slight expansion of the lower end connector 30 and/or a slight compression of the proximal end connector 24. Friction in conjunction with compressive forces allows the coupling to remain in place.

FIG. 5 also depicts embodiments where the inner diameter 44 of the intermediate portion 34 of the tracheal tube extension 26 has the same size as the inner diameter 46 of the tracheal tube 12. As mentioned earlier, such embodiments allow for minimal dead space in the airway management system 10 which in turn may lessen the WOB of a patient. Further, FIGS. 3, 4, and 5 all depict embodiments of the male proximal end connector 24 that may couple with a standard female connector, such as a 15 mm OD female connector that does not have any secure attachment features.

Figure 6:
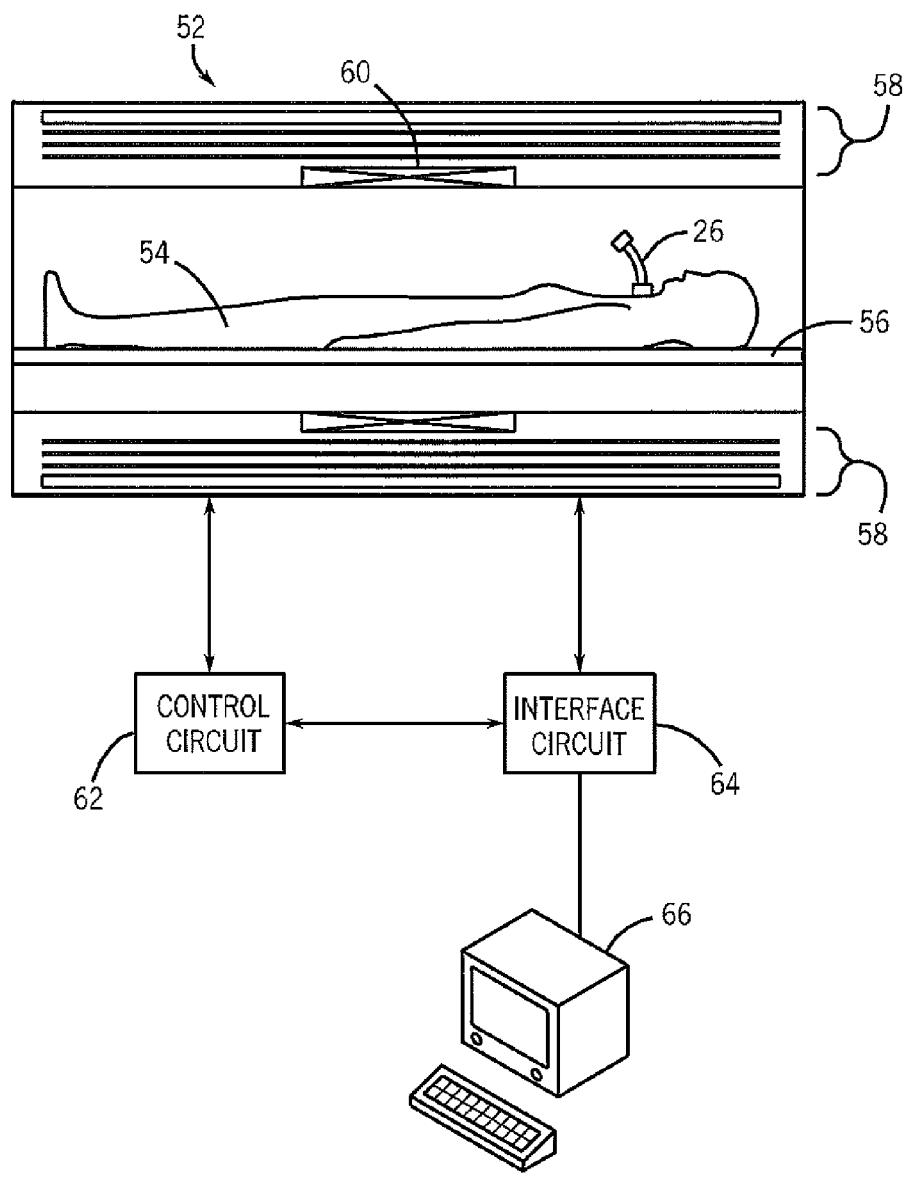
FIG. 6 illustrates an embodiment of a magnetic resonance imaging system and an embodiment of a tracheal tube extension.

Turning to FIG. 6, an exemplary embodiment of an MRI compatible tracheal tube extension 26 is illustrated as it may be used inside an MRI scanner 52. The MRI scanner 52 may be of any suitable type of rating, including scanners varying from 0.5 Tesla ratings to 1.5 Tesla ratings and beyond. As mentioned above, the tracheal tube extension 26 may include MRI compatible embodiments that allow for the patient to remain intubated while undergoing MRI procedures. The tracheal tube extension 26 may be manufactured of materials that do not distort or interfere with the imaging process of the MRI scanner 52. Some example materials that may be used in the manufacturing of the MRI compatible embodiments of the tracheal tube extension 26 include phthalate-free polyvinyl chloride (PVC), polyethylene terephthalate (PET), low-density polyethylene (LDPE), polypropylene, silicone, neoprene, and polyisoprene. Accordingly, some embodiments of the tracheal tube extension 26 may be MRI compatible, that is, the tracheal tube extension 26 may be used in the MRI scanner 52 without causing distortions or degradations in the resulting imagery.

A patient 54 may be intubated and the tracheal tube extension 26 may be coupled to, for example, a ventilator providing an artificial airway circuit. The patient 54 may then be placed on a table 56 which may position the patient 54 in a desired location inside the scanner 52 for scanning. The scanner 52 may include a series of associated coils for producing controlled magnetic fields, for generating radio frequency (RF) excitation pulses, and for detecting emissions from gyromagnetic material within the patient in response to such pulses. A series of gradient coils 58 are grouped in a coil assembly for generating controlled magnetic gradient fields during examination sequences. An RF coil 60 is provided for generating RF pulses for exciting the gyromagnetic material. In the embodiment illustrated in FIG. 6, the RF coil 60 also serves as a receiving coil. Thus, the RF coil 60 may be coupled with a control circuitry 62 in passive and active modes for receiving emissions from the gyromagnetic material and for applying RF excitation pulses, respectively. An interface circuitry 64 may be communicatively coupled with the control circuitry 62 and used to process the signals received through the scanning activities and to create the resulting images. The images may then be displayed in a computer workstation 66 or a monitor. The MRI procedure and the quality of the images obtained by using the scanner 52 remain unaffected when using MRI compatible embodiments of the tracheal tube 26.

It is to be understood that the tracheal tube extension 26 and the secure attachment features of the tracheal tube 12 may be used in tracheostomy tubes as well as in endotracheal tubes. Indeed, the embodiments disclosed herein may be used in any type of tracheal tube system.

What is claimed is:

1. A tracheal tube extension system comprising:
   an upper end connector configured to be coupled to a medical device;
   an intermediate portion coupled to the upper end connector; and
   a lower end connector coupled to the intermediate portion and configured to be coupled to a male connector of a tracheal tube, the lower end connector comprising an attachment feature that interfaces with a complementary feature of the male connector to removably secure the tracheal tube extension to the tracheal tube, wherein the attachment feature comprises a protrusion disposed on an interior wall of the lower end connector and configured to couple to a complementary recess disposed on an exterior wall of the male connector, wherein the complementary recess is disposed about the entire circumference of the male connector, wherein the lower end connector comprises a flexible proximal terminal portion configured to expand outwardly when a radial force is applied to the lower end connector for insertion or removal of the lower end connector from the tracheal tube.

2. The system of claim 1, wherein the intermediate portion of the tracheal tube extension comprises a flexible portion.

3. The system of claim 1, wherein the intermediate portion of the tracheal tube extension comprises a reinforced portion configured to prevent the tracheal tube extension from kinking.

4. The system of claim 1, wherein the intermediate portion comprises a length of at least 5 mm and an internal diameter of at least 2 mm.

5. The system of claim 1, wherein the male connector of the tracheal tube comprises an outer diameter of at least 5 mm.

6. The system of claim 1, wherein the protrusion comprises a barb-like extension.

7. The system of claim 1, wherein the protrusion comprises at least one peg-like extension, a ring-like extension, or a partial ring-like extension configured to couple to a groove in the male connector, and wherein the radial force is provided via the protrusion.

8. The system of claim 1, wherein the lower end connector comprises a at least one protruding member configured to be pulled outwardly by a user to facilitate rapid and toolless detachment of the lower end connector from the male connector, and wherein the radial force is provided via the at least one protruding member.

9. The system of claim 1, wherein the medical device comprises at least one of a ventilator, suctioning equipment, manual respirator, nebulizer, or vaporizer removably coupled to the upper end connector of the tracheal tube extension.

10. The system of claim 1, wherein the tracheal tube extension system is magnetic resonance imaging compatible.

11. A tracheal tube extension system comprising:
    a tracheal tube having a male connector on a proximal end thereof, the male connector having a first attachment feature; and
    a tracheal tube extension comprising an upper end connector configured to be coupled to a ventilator conduit, an intermediate portion coupled to the upper end connector, and a lower end connector coupled to the intermediate portion and configured to be coupled to the male connector of the tracheal tube, the lower end connector comprising a second attachment feature that interfaces with the first feature of the male connector to removably secure the extension to the tracheal tube,
    wherein the first attachment feature comprises a recess disposed on an exterior wall of the male connector and wherein the second attachment feature comprises a protrusion disposed on an interior wall of the lower end connector and configured to couple to the recess, wherein the lower end connector comprises at least one protruding member configured to be pulled outwardly by a user to detach the lower end connector from the male connector, and wherein the lower end connector comprises a flexible proximal terminal portion configured to expand outwardly when a radial force is applied to the lower end connector for insertion or removal of the lower end connector from the tracheal tube.

12. The system of claim 11, wherein the first attachment feature comprises at least one recess and the second attachment feature comprises at least one protrusion configured to enter into the recess when the tracheal tube extension is placed on the tracheal tube.

13. The system of claim 12, wherein the male connector is configured to receive a standard female connector of a medical device in place of the lower connector of the tracheal tube extension.

14. The system of claim 11, wherein the second attachment feature comprises at least one recess and the first attachment comprises at least one protrusion configured to enter in to the recess when the tracheal tube extension is placed on the tracheal tube.

15. The system of claim 11, wherein the tracheal tube extension system is magnetic resonance imaging compatible.

16. A tracheal tube extension system comprising:
    an upper end connector configured to be coupled to a ventilator conduit;

an intermediate portion coupled to the upper end connector and having an internal diameter; and a lower end connector coupled to the intermediate portion and configured to be coupled to a male connector of a tracheal tube having an inner diameter substantially the same as the internal diameter of the intermediate portion, wherein the lower end connector comprises a protrusion disposed on an interior wall of the lower end connector and configured to couple to a complementary recess disposed on an exterior wall of the male connector, and wherein the lower end connector comprises a flexible proximal terminal portion configured to expand outwardly when a radial force is applied to the lower end connector for insertion or removal of the lower end connector from the tracheal tube.

17. The system of claim 16, wherein the tracheal tube system is magnetic imaging compatible.

18. The system of claim 17, comprising at least one of a ventilator, suctioning equipment, manual respirator, nebulizer, or vaporizer coupled to the upper end connector.

19. A tracheal tube extension system comprising:

an upper end connector configured to be coupled to a ventilator conduit;

an intermediate portion coupled to the upper end connector and having an internal diameter; and, a lower end connector coupled to the intermediate portion and configured to be coupled to a male connector of a tracheal tube;

wherein the upper end connector, the intermediate portion and the lower end connector are made of one or more materials that do not adversely affect data collected via a magnetic resonance imaging system scanner, and wherein the lower end connector comprises a protrusion disposed on an interior wall of the lower end connector and configured to couple to a complementary recess disposed on an exterior wall of the male connector, wherein the complementary recess is disposed about the entire circumference of the male connector, and wherein the lower end connector comprises a flexible proximal terminal portion configured to expand outwardly when a radial force is applied to the lower end connector for insertion or removal of the lower end connector from the tracheal tube.

20. The system of claim 19, wherein the internal diameter of the intermediate portion substantially the same as the inner diameter of the tracheal tube.

21. The system of claim 19, wherein the tracheal tube comprises a tracheostomy tube or an endotracheal tube.

* * * * *